(12) United States Patent
Turrini et al.

(10) Patent No.: US 6,960,177 B2
(45) Date of Patent: Nov. 1, 2005

(54) BRACE FOR OSTEOARTHRITIC KNEE

(75) Inventors: Alberto Turrini, Castel d'Azzano (IT); Moreno Ferrigolo, Dossobuono (IT)

(73) Assignee: F.G.P. Srl, Dossobuono (IT)

( * ) Notice: Subject to any disclaimer, the term of this patent is extended or adjusted under 35 U.S.C. 154(b) by 0 days.

(21) Appl. No.: 10/503,694

(22) PCT Filed: Feb. 3, 2003

(86) PCT No.: PCT/IT03/00048

§ 371 (c)(1),
(2), (4) Date: Aug. 4, 2004

(87) PCT Pub. No.: WO03/065943

PCT Pub. Date: Aug. 14, 2003

(65) Prior Publication Data

US 2005/0159691 A1    Jul. 21, 2005

(30) Foreign Application Priority Data

Feb. 6, 2002    (IT) ............................... VR02A0006

(51) Int. Cl.[7] .............................................. A61F 5/00
(52) U.S. Cl. .............................. 602/26; 602/5; 602/16; 602/23; 128/882
(58) Field of Search ................................ 602/26, 5, 16, 602/19, 23; 128/846, 869, 882, 845; 606/53, 606/54

(56) References Cited

U.S. PATENT DOCUMENTS 4,489,718 A * 12/1984 Martin .......................... 602/16
4,531,515 A * 7/1985 Rolfes .......................... 602/16

(Continued)

FOREIGN PATENT DOCUMENTS

| AT | 144093 | 8/1994 |
|---|---|---|
| EP | 1 302 184 | 4/2003 |
| WO | WO 97/40789 | 11/1997 |
| WO | WO 00/18337 | 4/2000 |
| WO | WO 01/21114 | 3/2001 |
| WO | WO 01/45600 | 6/2001 |

OTHER PUBLICATIONS

International Search Report May 30, 2003.

*Primary Examiner*—Fadi H. Dahbour
(74) *Attorney, Agent, or Firm*—Charles Berman; Greenberg Traurig LLP

(57) ABSTRACT

A knee brace (10) consisting of an upper arch (12) positioned, when worn, above the knee and a lower arch (16) positioned, when worn, below the knee, connected to means of constraint for fixing to the limb, a first upright (13) equipped in its central part with a joint (15) consisting of a pair of respective rotating elements comprising toothed wheel portions prevented from reciprocally moving in a direction perpendicular to the axis of the brace, the first upright (13) presenting a first system designed to exert adjustable pressure on the knee joint and a second system designed to compensate the deformation of the first upright (13) in exerting this pressure, the first system consisting of a first micrometric angular hinge (20) positioned on the femoral part of the first upright (13) and a second micrometric angular hinge (21) positioned on the tibial part of the same upright (13), the brace having each of the respective rotating elements rigidly connected to a respective micrometric angular hinge element, and each micrometric angular hinge which is also rigidly connected to the second compensation system which is in turn connected to a respective femoral or tibial arch of the brace (10).

8 Claims, 3 Drawing Sheets

U.S. PATENT DOCUMENTS

| | | |
|---|---|---|
| 4,953,260 A | 9/1990 | Fargnier |
| 5,400,806 A | 3/1995 | Taylor |
| 5,415,625 A | 5/1995 | Cassford et al. |
| 5,641,322 A * | 6/1997 | Silver et al. .................. 602/26 |
| 5,658,241 A * | 8/1997 | Deharde et al. ............... 602/5 |
| 5,707,347 A * | 1/1998 | Bixler .......................... 602/26 |
| 5,823,931 A * | 10/1998 | Gilmour ....................... 602/26 |
| 6,402,711 B1 * | 6/2002 | Nauert ......................... 602/16 |
| 6,540,709 B1 * | 4/2003 | Smits ........................... 602/16 |
| 6,890,314 B2 * | 5/2005 | Seligman ..................... 602/26 |

* cited by examiner

BRACE FOR OSTEOARTHRITIC KNEE

TECHNICAL FIELD

The present invention concerns a brace for the treatment of knee joints affected by osteoarthritic type disorders, in particular for the medial and lateral adjustment and control of this joint.

The present invention also proposes to provide an easily adjustable brace that can be applied in all cases which require compensatory adjustment of the knee joint, as in cases of varus or valgus deformity of the knee and in general in cases of trauma to the knee joint.

The present invention can be applied in the medical industry with particular reference to manufacturers of prostheses and braces.

BACKGROUND ART

Arthrosis, or osteoarthritis, is a very common joint disorder which tends to worsen with time.

Onset occurs when, for a variety of reasons, the articular cartilage is no longer able to resist the continuous stresses during the movement of the limbs.

The insufficiency of the cartilage may be due to age, excess weight which overloads the joint, hereditary factors or environmental factors (climate, etc.).

The joints most frequently affected are the hip, the knee, the vertebral column and all joints affected by former injuries; symptoms are initially mild and often intermittent.

Pain is characteristic: in the morning it is intense, improving during the day and becoming worse again towards the evening. As the disease progresses, pain becomes continual.

Another symptom is the reduction in movement which may even lead to immobilisation.

The probability of developing more or less serious forms of arthritis occurs in particular in subjects with varus or valgus deformity of the knee. In these subjects, especially when elderly, the cartilage of the knee joint becomes worn and the joint is chronically or acutely inflamed.

A specific brace for a knee affected by arthrosis must first of all be capable of enveloping the joint, following the individual conformation of the limb, and of providing medial or lateral thrust which opposes the pathological unbalancing of the load.

This can be achieved by applying, for example, pressure which alters the contact between the opposite condyles of the knee bone, reducing the pressure on the condyles and limiting the pain.

Some solutions known to background art foresee the use of flexible hinges which are fitted to the side arms of the structure, making it possible to adjust the brace at the joint both laterally and medially.

For example, the document U.S. Pat. No. 5,400,806 describes a brace with a hinge positioned on the side part of the structure at the level of the joint, capable of tilting the femoral and tibial arms of the side upright at a certain angle, thus applying a force perpendicular to the axis of the leg.

The document WO-A-97/40789 presents another example of a brace with angular compensation hinges which can be adjusted to modify the medial or lateral thrust force exerted by the brace at the knee joint.

The technical solution described is not without disadvantages, the first being the fact that the angular stress exerted by the hinges fitted to the structure of the brace is concentrated on the joint which allows movement of the femur with respect to the tibia, making it particularly delicate from a mechanical point of view.

Furthermore, the side upright is completely rigid, excluding the use of a second upright in the structure of the brace as the normal variations in knee volume during walking would cause the knee to be compressed.

On the other hand, the use of two uprights in structures of this type of brace is usually preferred due to the stability and control that they provide.

The document WO-A-01/45600 describes a brace with a hinged joint structure which comprises a part supporting the joint, a first gear portion supported during rotation, in relation to the part supporting the joint and with gear teeth on one portion. The first gear portion is coupled by rotation to the upper support arm of the brace and has a joint surface adjacent to the surface of the support arm.

A second portion of the gear, also supported during rotation by the same support part and having the same structure as the first portion, is coupled by rotation to the lower arm of the brace.

The joint surfaces of the first and second gear portion as described in WO-A-01/45600 are configured in such a way as to allow a predetermined medial/lateral articulation angle of the upper and lower arms, keeping the two portions of the gear on the same plane.

One upright also presents hinges which can be micrometrically adjusted to allow tilting of the upper and lower arms of the upright leading to a perpendicular thrust force on the limb axis.

The main disadvantages of the brace described in WO-A-01/45600 concern the overall dimensions of this hinged joint at the sides of the brace, since the curvature of the limbs in subjects with osteoarthritis is already particularly accentuated and can even be problematic in those with valgus deformity of the knee.

The system which connects the uprights to the central joint and the two parts presenting the gear teeth are also particularly delicate and easily subject to seizure since most of the force exerted by the joint during walking is concentrated on these parts and because they present a considerably extensive interconnecting and friction surface.

Finally, the uprights are rigid and cannot adapt to the anatomical structure of the limb and of the knee joint, nor to its physiological variations in volume during walking, this effect being particularly negative with the flexion between the femur and the tibia causing compression of the knee, less fluid movements and consequently less steady walking.

DESCRIPTION OF THE INVENTION

The present invention proposes to provide a knee brace, in particular for arthritic or osteoarthritic knees, which can eliminate or significantly reduce the drawbacks described above.

The present invention also proposes to provide a brace which is easy to adjust, even by the user, and which thanks to the presence of side uprights adaptable to the structure of the limb and the knee joint during flexion provides an appropriately controlled force at the knee, perpendicular to the axis of the leg, in such a way to exert a thrust force which alters the contact between the opposite condyles of the knee bone, reducing the pressure exerted on these condyles and limiting the pain.

This is achieved by means of a knee brace with the features described in the main claim and which can be applied in particular in osteoarthritic disorders of the knee.

The dependent claims describe advantageous forms of embodiment of the invention.

According to an advantageous form of embodiment of the invention, the knee brace comprises a frame consisting of an upper arch positioned, when worn, above the knee and a lower arch positioned, when worn, below the knee, connected to means of constraint for fixing to the limb, a first and second upright equipped respectively with an articulated joint in the central part, this articulated joint consisting of elements having a toothed wheel portion and which cannot move in a direction perpendicular to the axis of the limb.

The first upright presents a system designed to exert pressure on the knee joint and a system designed to compensate the deformation of the upright in exerting this pressure.

The second upright presents an elastically deformable system for adaptation of the rigid central articulated joint to the knee joint.

According to the present invention, the parts comprising the articulated joint remain more or less on the same plane during the thrust action of the upright on the joint.

According to a particularly advantageous form of embodiment of the present invention, the joint comprises two rotation pins with a pair of toothed wheel portions designed to engage with each other and respectively connected with the upper and lower part of the upright.

The portions of toothed wheel are kept on the same plane by metal support plates which prevent any movement of these parts in a direction perpendicular to the longitudinal axis of the brace upright.

A further embodiment according to the invention foresees the use of a polycentric articulation with four pins which allows an eccentric type rotation of the uprights; in this case too the toothed wheel portions of the articulation are rigidly maintained on the same plane.

According to the invention, a brace upright presents a pair of micrometric angular adjustment hinges of the type which are the subject of the international patent application no. WO-A-01/21114 in the name of the applicant hereto, which allow fine adjustment of the pressure on the knee joint in cooperation with at least one portion of the elastically deformable upright, the upper or lower part with respect to the knee.

This pressure is exerted on the knee joint at the level of the brace joint by a condyle plate connected to it and in contact with the side of the knee.

According to a particularly advantageous form of embodiment of the present invention, the elasticity of the uprights working together and in response to the thrust perpendicular to the joint is achieved by inserting elastic and/or flexible elements which integrate to form a whole with the upper and lower portions of the uprights and/or with the use of a flexible hinge according to the invention.

The elastic elements can consist of steel plates or sectors in composite plastic material.

The elastic hinge according to one embodiment of this invention consists of two essentially flat portions, upper or lower, of an upright, connected to each other by fixing means such as rivets for example and presenting an overlapping area.

Elastic means such as Belleville washers for example are inserted in the overlapping area between the two parts of the upright or on the outer surface of this area.

A pin, acting as a separator and a guide, is also inserted between the two portions of the hinge which overlap each other.

Furthermore, according to an advantageous embodiment, the side upright of the frame opposite the upright exerting the transverse force obtained by the action of the micrometric angular hinges is in turn elastic thanks to the insertion of the said elements or flexible hinges, in order to make the brace adaptable to the shape of the limb and providing a high degree of stability and effective control of the knee joint movement.

DESCRIPTION OF THE DRAWINGS

Other features and advantages of the invention will become evident on reading the following description of one embodiment of the invention, given as a non-binding example, with the help of the enclosed drawings, in which.

DESCRIPTION OF ONE EMBODIMENT

In the figures, the reference number 10 generally indicates a knee brace, in this case a brace 10 which can be applied in disorders of osteoarthritic knees.

Figure 1:
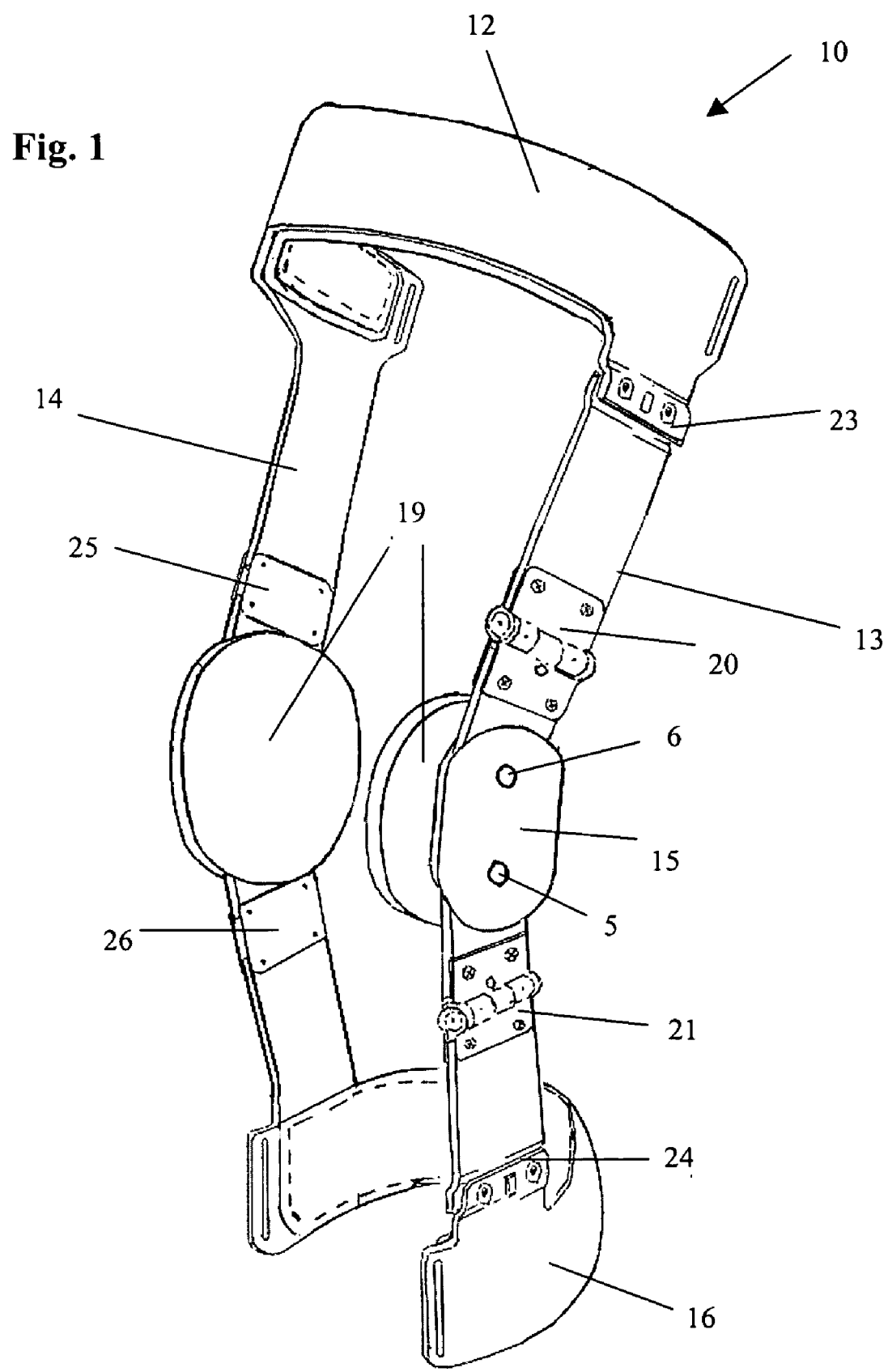
FIG. 1 shows a perspective side view, slightly from above, of a knee brace according to the invention.

According to a particular embodiment of the invention shown in FIG. 1, the brace 10 consists of an upper arch 12 positioned, when worn, above the knee and a lower arch 16 positioned, when worn, below the knee, connected to means of constraint for fixing to the limb, a first upright 13 and a second upright 14 equipped respectively with a joint 15 in the central part consisting of rotating joint elements which are however prevented from moving perpendicular to the longitudinal axis of the brace.

According to a particular embodiment, the first upright 13 presents a system designed to exert pressure on the knee joint and consisting of micrometric angular hinges 20, 21 in which a first hinge 20 is positioned on the femoral part of the upright and a second hinge 21 is positioned on the tibial part of the same upright.

By adjusting the flexion of the upright portion connected to the joint 15 by means of the hinges 20, 21, it is possible to apply pressure on the knee.

It should be emphasised that according to this invention the elements forming the joint 15 do not move in a direction perpendicular to the rotation axis of hinges 20,21, due to the action exerted by the hinges themselves.

In cooperation with the system of micrometric hinges 20, 21, the upright 13 is equipped with a system designed to compensate the deformity of the upright and to follow the shape of the limb, this system consisting of a first flexible hinge 23 positioned on the femoral part of the upright 13 and a second flexible hinge 24 positioned on the tibial part of the same upright.

To balance the thrust of the upright 13, and thus prevent compression of the knee joint, according to a particular embodiment of the invention the upright 14 is equipped with elastic elements 25, 26 on the femoral and tibial parts of the upright respectively.

These elements 25, 26 can consist of elastic plates made from steel or composite plastic material.

According to a further form of embodiment, not shown in the drawings, these elements 25, 26 are replaced by flexible hinges of the type described above with reference to the hinges 20 and 21.

Figures 2, 3:
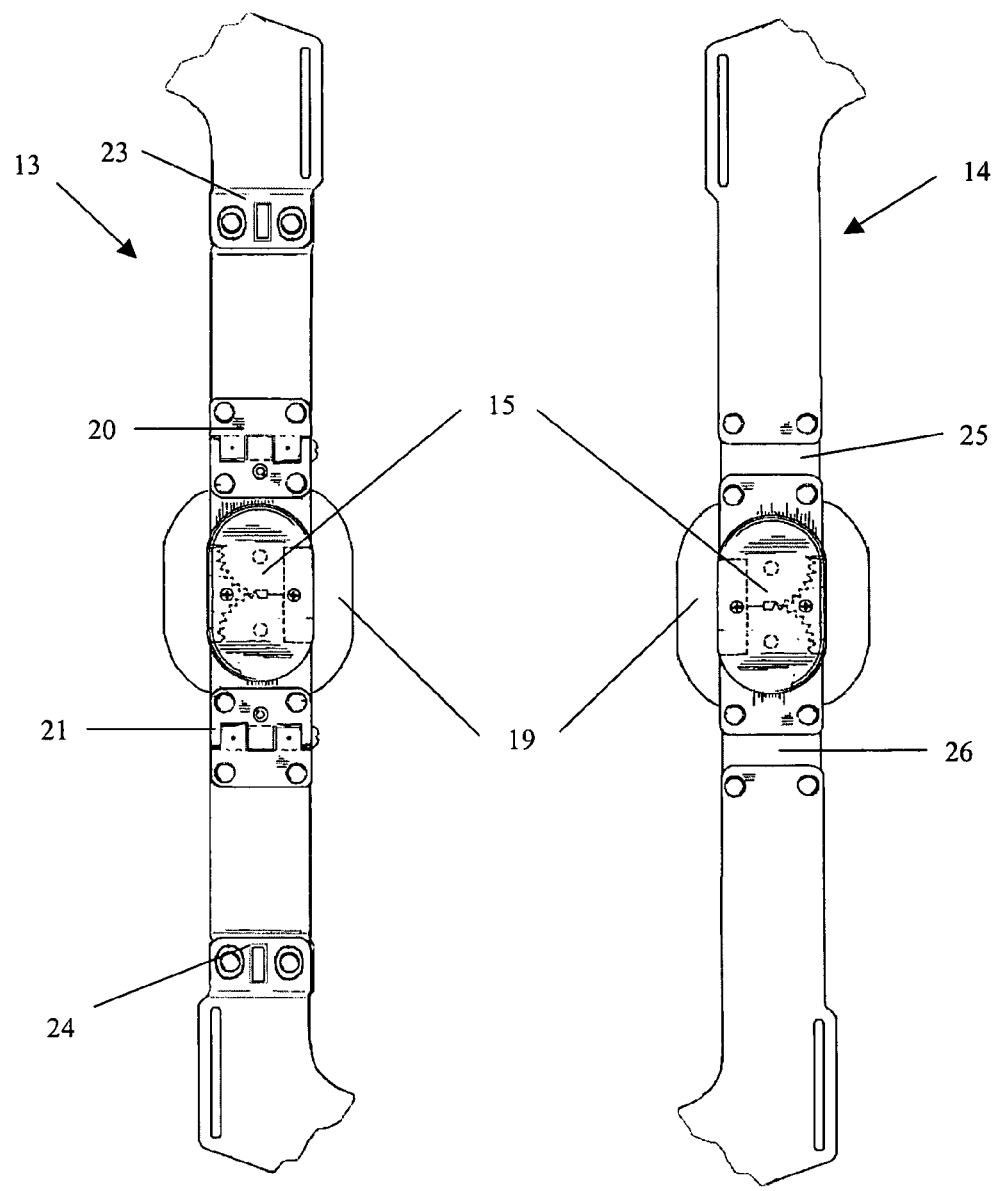
FIG. 2 shows a front view of one of the elastically deformable side uprights according to the invention, with micrometrical angular hinges and flexible hinges.
FIG. 3 shows a front view of one of the elastically deformable side uprights according to the invention, which can be associated with the upright in FIG. 1, presenting only elastic elements.

The two uprights 13 and 14 are shown respectively in FIG. 2 and in FIG. 3 in which the joints 15 consist of two toothed wheel portions designed to engage with each other.

In the form of embodiment shown in FIG. 2 the toothed wheels are respectively constrained to hinges 20, 21, while in the embodiment shown in FIG. 3 the toothed wheels are respectively constrained to the elastic plates 25, 26.

These toothed wheel portions rotate on two pins and are kept in place by two metal plates fitted on opposite sides of these toothed wheel portions.

The joint 15 is thus rigid as its components are prevented from moving in a direction perpendicular to the axis of the brace.

According to a particular embodiment of the invention (not shown in the drawings), the central joint 15 can be the polycentric type with four pins, which causes an eccentric movement of the uprights, in a way already known to the background art.

In the light of recent tests carried out by the applicant, analysing the movement of the limb and of the brace during walking, the application of this type of joint is particularly advantageous, keeping the brace 10 in position for longer and preventing lowering of the brace due to slipping down the leg.

The rigid joints 15 present a condyle plate 19 designed to come into contact with the knee joint, uniformly transmitting the force exerted by the elastically deformable side upright on the joint, and to contain and support this joint.

According to an advantageous embodiment of the invention, these condyle plates, or at least one of the two, can consist of an adjustable pneumatic system in order to ensure optimum adjustment of the pressure and a reasonable degree of comfort for the person wearing the brace.

Figure 4:
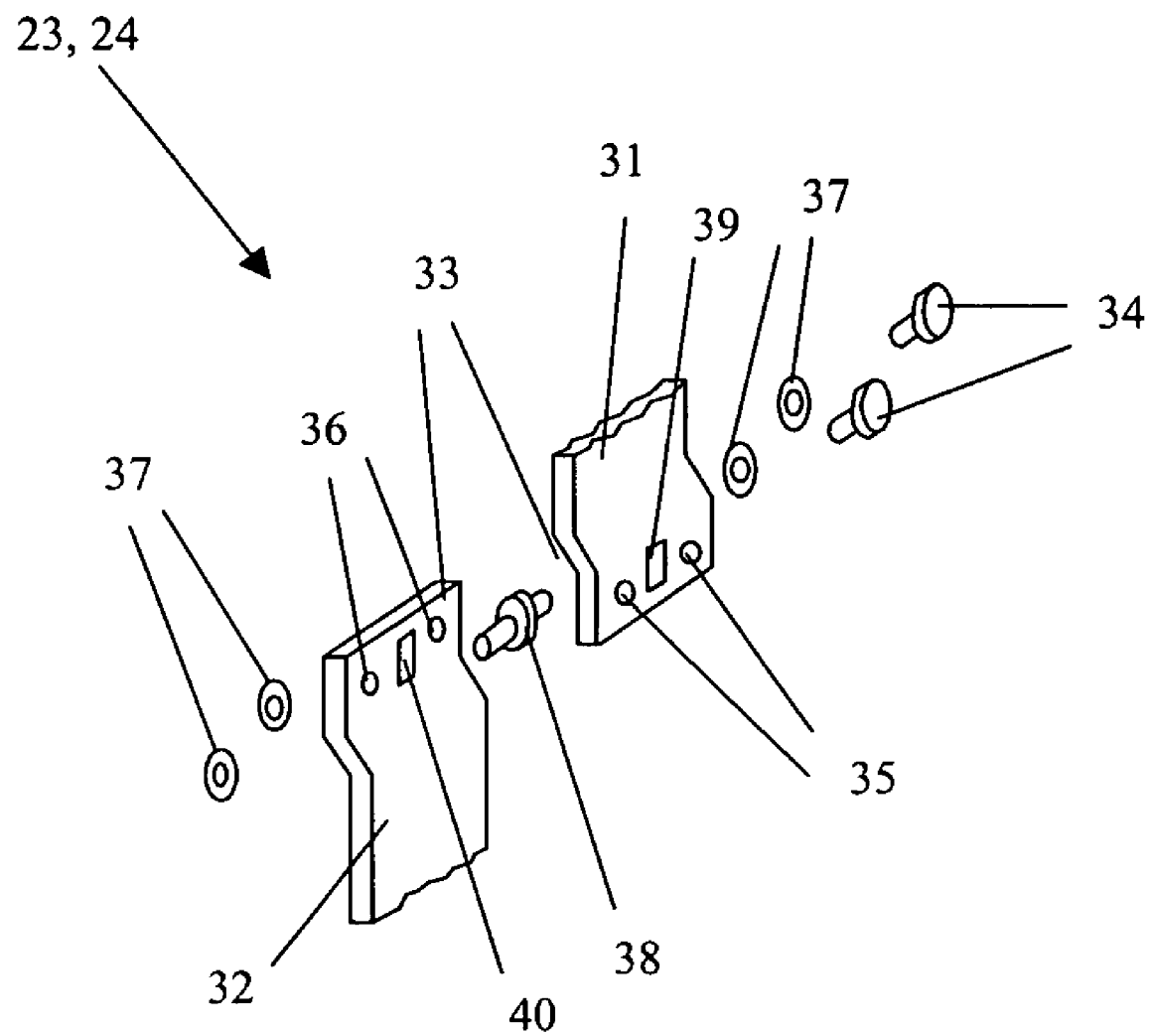
FIG. 4 represents an exploded view of a flexible hinge according to the invention.

FIG. 4 shows a flexible hinge 23, 24 according to the invention, consisting of two portions of an upright, a first portion 31 integral with or forming a single piece with one of the arches 12, 16 and a second portion 32 constrained to a respective micrometric hinge 20, 21, connected in turn to the joint 15.

The respective portions 31, 32 of the flexible hinge 23, 24 presenting an overlapping area 33 and are constrained to each other by fixing means 34, such as rivets for example, through relative holes 35, 36 in correspondence with which elastic means 37, for example steel Belleville washers, are also inserted.

According to this embodiment, at the level of the overlapping area 33 between the two parts of the upright 31, 32, a pin 38, designed to act as a separator and a guide, its central portion having a greater diameter, is inserted in relative slots 39, 40 situated one in front of the other on the two respective components of the hinge.

Another form of embodiment of the flexible hinges 23, 24, not shown in the drawings, foresees the insertion of elastic means 37 in the overlapping area of the two parts 31, 32 of the upright.

The use of these flexible hinges 23, 24, in cooperation with the micrometric angular hinges 20, 21 on the upright 13 allows the user to adjust the pressure of the brace 10 at the level of the knee joint in a controlled way in relation to the flexion of the joint itself.

The pressure and support of the brace are in fact greatest during extension of the leg, i.e. when the joint supports most of the load, while it exerts minimum constraint when the limb is flexed.

The invention is described above with reference to a number of preferred forms of embodiment.

It is nevertheless clear that the invention is susceptible to numerous variations within the framework of technical equivalents.

By way of example, embodiments are foreseen according to which the brace is equipped with a single side upright fitted with micrometric hinges and flexible hinges.

What is claimed is:

1. A knee brace (10) comprising an upper arch (12) positioned, when worn, above the knee and a lower arch (16) positioned, when worn, below the knee, connected to means of constraint for fixing to the limb, a first upright (13) equipped in its central part with a joint (15) consisting of a pair of respective rotating elements comprising toothed wheel portions prevented from reciprocally moving in a direction perpendicular to the axis of the brace, the first upright (13) comprising a first system suitable for exerting an adjustable pressure on the knee joint and a second system suitable for compensating the deformation of the first upright (13) in exerting this pressure, the first system consisting of a first micrometric angular hinge (20) positioned on the femoral part of the first upright (13) and a second micrometric angular hinge (21) positioned on the tibial part of the same upright (13), whereby each of the respective rotating elements is rigidly connected to a respective micrometric angular hinge element, and whereby each micrometric angular hinge is also rigidly connected to the second compensation system, which is in turn connected to a respective femoral or tibial arch of the brace (10), wherein in exerting pressure on the knee joint, the system compensating the deformation of the first upright (13) consists of a first flexible hinge (23) positioned on the femoral part of the upright (13) and a second flexible hinge (24) positioned on the tibial part of the same upright.

2. A brace according to claim 1, wherein the respective rotating elements comprising toothed wheel portions are held in place by metal support plates.

3. A brace according to claim 1, wherein the joint (15) of the uprights (13, 14) is the polycentric type with four pins, allowing an eccentric type rotation movement of the femoral and tibial portions of the uprights (13, 14).

4. A brace (10) according to claim 1, wherein the joint (15) comprises a condyle plate (19) suitable for coming into contact with the knee joint.

5. A brace (10) according to claim 4, in which said condyle plate comprises an adjustable pneumatic system.

6. A brace (10) according to claim 1, further comprising a second upright (14) connected to said arches on the opposite side with respect to the first upright (13).

7. A brace (10) according to claim 6, wherein the second upright (14) comprises an elastically deformable system consisting of a first elastic and/or flexible element (25) positioned on the femoral part of the upright and of a second elastic and/or flexible element (26) positioned on the tibial part of the same upright.

8. A brace according to claim 7, wherein the elastic and/or flexible elements (25, 26) consist of steel plates or composite plastic material sectors.

* * * * *